US009565920B2

(12) United States Patent
Thorpe et al.

(10) Patent No.: US 9,565,920 B2
(45) Date of Patent: Feb. 14, 2017

(54) APPLICATOR DEVICE OR DISPENSER WITH APPLICATOR TIP ASSEMBLY (71) Applicant: HCT ASIA LTD., Central (HK)

(72) Inventors: Timothy Thorpe, Santa Monica, CA (US); Adrian Charles Apodaca, Daly City, CA (US); Denis Pierre Maurin, Los Angeles, CA (US); Armando Villarreal, Los Angeles, CA (US)

(73) Assignee: HCT ASIA LTD., Central (HK)

( * ) Notice: Subject to any disclaimer, the term of this patent is extended or adjusted under 35 U.S.C. 154(b) by 746 days.

(21) Appl. No.: 13/840,889

(22) Filed: Mar. 15, 2013

(65) Prior Publication Data

US 2014/0234004 A1 Aug. 21, 2014

Related U.S. Application Data (60) Provisional application No. 61/766,645, filed on Feb. 19, 2013.

(51) Int. Cl.
*A45D 31/00* (2006.01)
*A45D 40/26* (2006.01)
(Continued)

(52) U.S. Cl.
CPC .............. *A45D 40/26* (2013.01); *A45D 34/04* (2013.01); *A45D 34/041* (2013.01);
(Continued)

(58) Field of Classification Search
CPC ..................... A45D 2200/15; A45D 2200/155; A45D 2200/157
See application file for complete search history.

(56) References Cited

U.S. PATENT DOCUMENTS 8,573,874 B2* 11/2013 Neuner ................. A45D 34/04
401/261
8,864,401 B2* 10/2014 Duru ..................... A45D 34/04
401/1
(Continued)

FOREIGN PATENT DOCUMENTS

GB 2449141 A 11/2008

OTHER PUBLICATIONS

International Search Report mailed Apr. 22, 2014 in corresponding International Patent Application No. PCT/US2014/017021.

*Primary Examiner* — Joshua Wiljanen
(74) *Attorney, Agent, or Firm* — Seager, Tufte & Wickhem LLP (57) ABSTRACT An applicator device or dispenser includes an applicator tip assembly and a housing which may, in some examples, have a reservoir for containing a product, such as a cosmetics product or a medicinal product. The applicator tip assembly may be coupled to the housing and may comprise a thermal storage applicator portion having an application face for applying the product to a surface, the thermal storage applicator portion being made from a material that is capable of storing and retaining and/or transferring thermal energy during application of the product. The applicator tip assembly may further comprise a main body portion having a product delivery passageway extending through the main body portion for dispensing a product to the application face of the thermal storage applicator portion, the main body portion configured to at least partially enclose the thermal storage applicator portion at a periphery of the thermal storage applicator portion.

28 Claims, 8 Drawing Sheets (Section A-A)

(51) Int. Cl.
*A61M 35/00* (2006.01)
*A45D 34/04* (2006.01)
(52) U.S. Cl.
CPC ... *A61M 35/003* (2013.01); *A45D 2200/1054* (2013.01); *A45D 2200/15* (2013.01); *A45D 2200/155* (2013.01)

(56) References Cited

U.S. PATENT DOCUMENTS

| | | | |
|---|---|---|---|
| 2009/0062815 A1 | 3/2009 | Karasiuk | |
| 2011/0123252 A1* | 5/2011 | Thorpe | A45D 34/04 401/266 |
| 2011/0190672 A1 | 8/2011 | Apodaca | |

* cited by examiner

FIG. 3B (Section A-A)

FIG. 7A (Section A-A)

FIG. 7B (Section A-A)

FIG. 7C (Section A-A)

FIG. 8

APPLICATOR DEVICE OR DISPENSER WITH APPLICATOR TIP ASSEMBLY

CROSS REFERENCE TO RELATED APPLICATIONS

This application is based on and claims priority to U.S. Provisional Application No. 61/766,645, filed on Feb. 19, 2013, by Thorpe et al., entitled, "Applicator Device or Dispenser with Stone Tip," the contents of which are herein incorporated by reference.

BACKGROUND

Devices exist for dispensing cosmetic or medicinal products. Such devices usually consist of an outer tubular shell or housing, a delivery mechanism for displacement of the cosmetic or medicinal products, and an applicator tip. For example, in the medical industry, applicators are employed for applying medicinal products, such as ointments, to portions of the body. In the cosmetics and personal care industries, applicators are used to apply lipstick, lip balm, skin creams, lotions, and other cosmetic products to portions of the body.

In many cases, these medicinal and cosmetic products may include skin care substances, such as aloe or lanolin, that provide a healing or therapeutic effect to heal damaged skin or maintain healthy skin. In addition, these products may include therapeutic substances, such as topical anesthetics, analgesics, fragrances, menthol, or other substances that provide a soothing or stimulating sensation when applied to skin of a user of the product. In addition to skin care substances, thermal treatments (e.g., application of heat and/or cold) are known to relieve pain, provide a therapeutic sensation, and to slow the body's natural response to injury so that a slower and more controlled healing process may ensue.

Existing cosmetic and medicinal dispensers are limited to application of products to the skin, and do not provide for thermal treatments of the skin. Accordingly, there remains a need in the art for improved dispensers.

SUMMARY

This summary is provided to introduce simplified concepts of applicators and dispensers with applicator tip assemblies, which are further described below in the Detailed Description. This summary is not intended to identify essential features of the claimed subject matter, nor is it intended for use in determining the scope of the claimed subject matter.

This disclosure is directed to application devices, implements, or dispensers with applicator tip assemblies having thermal capacities, which are capable of storing and retaining thermal energy and/or transferring thermal energy. The applicator tip assemblies may allow a product to be applied locally or topically to a selected area of a surface.

In some implementations, a housing may be coupled to the applicator tip assembly and may have a reservoir for product storage. The applicator tip assembly may have a thermal storage applicator portion having an application face for applying the product to the user's skin. Suitable housings include tubes, bottles, tottles, and other containers.

In some implementations, the thermal storage applicator portion of the applicator assembly may comprise a material capable of storing and retaining thermal energy and/or transferring thermal energy that can be heated or cooled and are able to retain or transfer the heated or cooled condition for a period of time.

In still further implementations, the applicator tip assembly may include a main body portion having a product delivery passageway extending through the main body portion for dispensing a product to the application face of the thermal storage applicator portion. The main body portion may be configured to at least partially enclose the thermal storage applicator portion at a periphery of the thermal storage applicator portion.

In some embodiments, the main body portion may be integrally formed with the housing or may be coupled thereto such as by injection molding the main body to a tube. Those of skill in the art will readily appreciate the appropriate techniques for coupling the main body to the housing.

Some embodiments provide an applicator tip assembly comprising a main body portion adapted to be coupled to a housing and comprising a product delivery passageway extending through the main body portion to convey a product stored in the housing, and a thermal storage applicator portion coupled to the main body portion and enclosed by the main body portion at a periphery of the thermal storage applicator portion, the thermal storage applicator portion having an application face for applying the product to a surface.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Overview

This disclosure is directed to dispensers with applicator tip assemblies that are able to transfer and/or store and maintain a level of thermal energy. The applicator tip assemblies may include a thermal storage applicator portion having an application face and comprising various metals, ceramics, stone materials, rock, gemstone, imitation gemstone, glass stone, volcanic stone, or composites thereof, whether natural or synthetic, that can be heated or cooled and are able to retain and/or transfer the heated or cooled condition for a period of time. More importantly, in some embodiments, due to the choice of materials and the relative size of the thermal storage applicator portion, the thermal storage applicator portions has the ability to convey a sensation of warming or cooling, and can regenerate that ability without external heating or cooling, other than exposure to ambient conditions. The applicator portion defines an application surface and a bore, through which product may be dispensed. A product may be dispensed from the dispenser through the applicator tip assembly for application to a surface such as, for example, a user's skin. By virtue of the thermal retention or transfer of the thermal storage applicator portion, thermal energy may be applied to the dispensed product so that it may be heated or cooled during application. Moreover, the application face of the thermal storage applicator portion may transfer heat to or from the user's skin, thereby causing the user to feel a thermal sensation (warm or cool depending on the thermal energy in or transferred via the thermal storage applicator portion). In some cases, the heat or cold transfer may also minimize or alleviate pain or discomfort caused by damage to the skin or other surface.

The choice of material for the thermal storage applicator portion will be chosen because of its ability to convey a thermal property to the skin of the user. In most instances, the thermal storage applicator portion will convey a cooling sensation to the skin. Due to its thermal properties, size, and shape, the thermal storage applicator portion will convey this cooling sensation, in theory, by absorbing some heat from the user's skin. As the tip warms, the cooling property can be regenerated simply by removing the tip from the skin. A relatively quick return to ambient temperature will restore the thermal storage applicator portion's cooling capability. Of course, the thermal storage applicator portion will regain some of its cooling ability even before it returns to ambient temperatures. Other important properties of the thermal storage applicator portion include but are not limited to its size (mass and/or volume), surface characteristics, and its porosity.

Suitable thermal storage materials include metals, such as but not limited to aluminum, titanium, steel, nickel, tin, copper, brass, platinum, alloys thereof. In some embodiments, the alloy ZAMAK (or ZAMAC) may be used. In others, stainless steel may be used.

In some embodiments, thermal storage material may be stone material. While features of various illustrative implementations are described, in other implementations, the thermal storage applicator portion may be configured in any form suitable for the application of the product to be dispensed. For example, the thermal storage applicator portion may be constructed in any suitable shape and size and may have any suitable mass, volume, and/or surface treatment desired for a given application.

As used herein the term "stone" or "stone material" means any stone, rock, mineral, ore, gemstone, imitation gemstone, glass stone, volcanic stone or composites thereof whether naturally occurring or synthetic. For example, river stone is a naturally occurring stone that may be used in some embodiments.

Examples of suitable stone materials include, without limitation, imitation gemstone, glass stone, volcanic stone, choral stone, metallic stone or ore, magnetic stone, concrete, composites, or the like.

For purposes of this specification, the term "glass stone" is meant to include natural and man-made forms of glass.

Exemplary mineral gemstones include but are not limited to agate, alexandrite, amethyst, ametrine, apatite, aventurine, azurite, beintoite, beryl, bloodstone, carnelian, chrysoberyl, chrysocolla, citrine, diamond, diopside, emerald, falcon's eye, fluorite, garnet, heliotrope, hematite, hiddenite, iolite, jade, white jade, jasper, red jasper, labradorite, lapis lazuli, larimar, malachite, marcasite, moonstone, morganite, obsidian, onyx, opal, peridot, quartz, rock crystal, rose quartz, ruby, sapphire, selenite, sodalite, spinel, sunstone, tanzanite, tiger's eye, topaz, tourmaline, turquoise, yogo sapphire, and zircon. In some embodiments, one or more of diamond, hematite, jade, moonstone, rock crystal, ruby or sapphire may be used. In some embodiments, jade is used, including green jade, white jade, and/or colored jade In other embodiments, rock crystal may be used. Regardless of the choice of gemstone, any color or quality may be used.

Organic gemstones include but are not limited to abalone, amber, ammolite, copal, coral, ivory, jet, pearl, and nacre. In some embodiments, pearl may be used.

Synthetic gemstones include but are not limited to, cubic zirconia, moissanite, synthetic diamond, synthetic ruby, synthetic sapphire, synthetic emerald, and composite gemstones.

Stone, other than gemstones listed above, includes but is not limited to stone or rock such as soapstone, granite, marble, river rock, river stones, pebbles, metallic stone/ores (germanium for example), volcanic stone, engineered/composite stone, or synthetic stone.

Engineered, composite or synthetic stone can be made from one or more stones or stone powders which are bound together. As an example, concrete is made with aggregate stone material and binders. Concrete can be formed into many shapes via molding, cutting, grinding, etc. and even polished. Other engineered, composite, and synthetic stone is readily available, or can be custom made with stone materials of choice.

The thermal storage applicator portion may be formed of any combination of materials to achieve the desired results, and may be subject to one or more finishing steps. For examples, it may be subjected to one or more secondary or finishing operations, such as buffing, polishing, chroming or electroplating, for example.

A main body portion of the applicator tip assembly may at least partially enclose the thermal storage applicator portion around a periphery of the thermal storage applicator portion. Furthermore, the thermal storage applicator portion may be substantially flat and disk-shaped, and is configured to couple to the main body portion. The configuration of the applicator tip assembly disclosed herein facilitates simplified manufacturing of the component parts of the applicator tip assembly by eliminating the need for more complex and/or costly manufacturing processes. For example, the thermal storage applicator portion may comprise metal and may be manufactured using a stamping process where secondary or finishing steps may be omitted due, at least in part, to a main body portion that at least partially encloses the thermal storage applicator portion.

The applicator tip assembly may be coupled to a housing such as a tube, bottle, tottle or other container for storing product. The main body of the applicator tip assembly may be integrally formed with the housing, or made separately and coupled to the housing such as by injection molding. In some embodiments, the applicator tip assembly may be made separate of the housing and coupled thereto in a later operation.

Illustrative Dispenser with Applicator Tip Assembly

Figure 1:
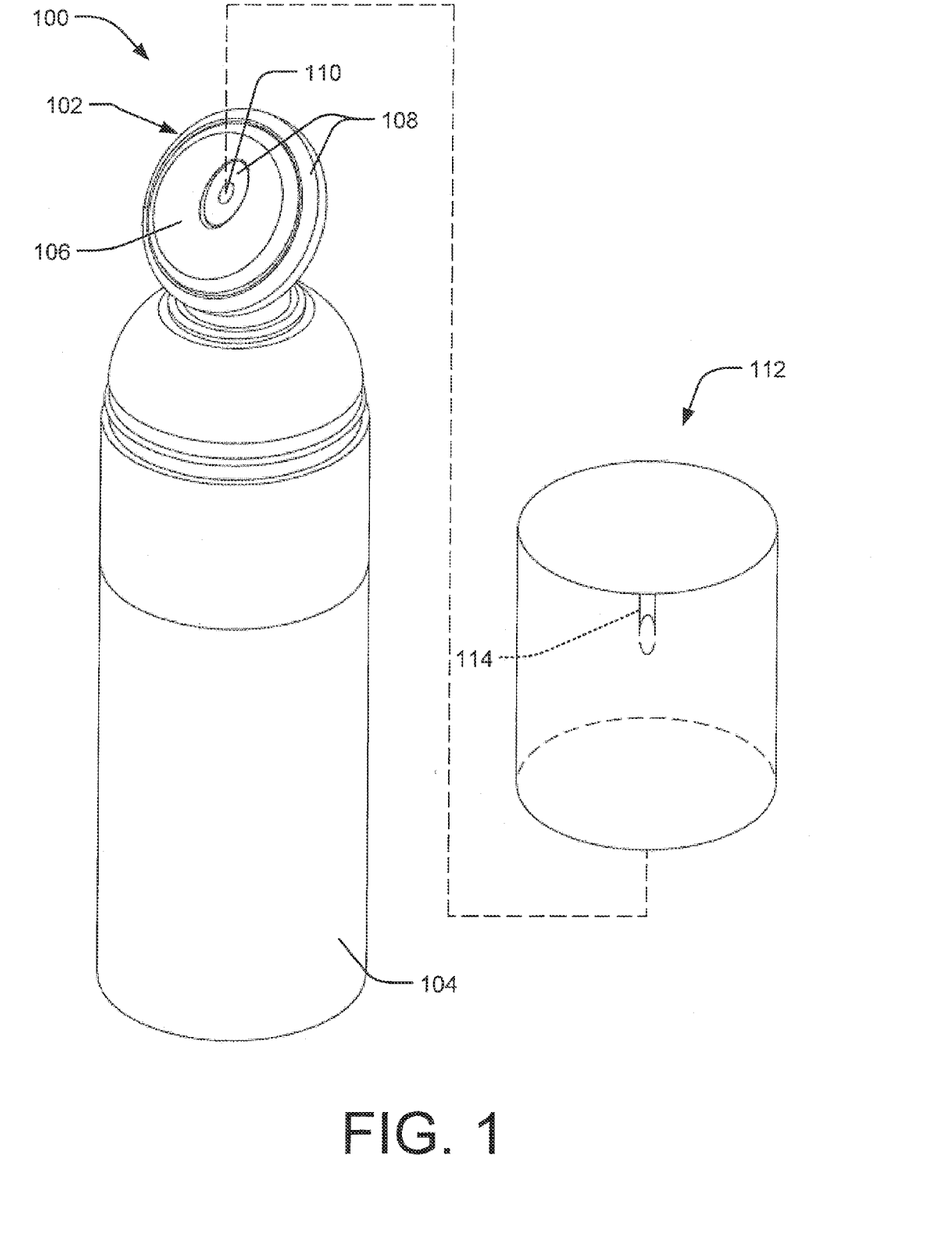
FIG. 1 is a perspective view of an illustrative dispenser with an example applicator tip assembly according to one implementation.

FIG. 1 represents an illustrative dispenser 100 with an applicator tip assembly 102 and a housing 104, or reservoir. In this implementation, the applicator tip assembly 102 is generally disk-shaped and comprises an applicator portion 106 made of a material capable of holding and retaining a thermal charge. In this sense, the applicator portion is sometimes referred to herein as a "thermal storage applicator portion" 106. In one implementation, the applicator portion 106 can be made of a metal such as, for example, stainless steel or ZAMAC alloy. However, in other implementations, any suitable material may be used that is capable of transferring or retaining heat or cold during the application of the product. Examples of other suitable materials include, without limitation, ceramic, stone materials, rock materials, gemstone, imitation gemstone, glass stone, volcanic stone, choral stone, metallic stone or ore, magnetic stone, concrete, composites, or the like. For purposes of this specification, the term "glass stone" is meant to include natural and man-made forms of glass. Suitable gem stones include, but are not limited to, agate, amethyst, aquamarine, diamond, emerald, garnet, jade, obsidian, onyx, opal, pearl, quartz, ruby, sapphire, topaz, and turquoise. While certain applicator portions are described herein as being capable of transferring or retaining heat or cold during the application of the product, in other embodiments, applicator portions according to this disclosure need not necessarily be capable of transferring or retaining heat or cold during the application of the product. For instance, thermal storage applicator portions according to embodiments of this disclosure may completely or partially comprise a porous or aerated stone or aggregate material (e.g., pumice or other volcanic stone, aerated concrete, etc.).

According to certain embodiments, the applicator portion 106 may comprise metals (e.g., zinc, aluminum, magnesium, titanium, steel, nickel, tin, copper, brass, platinum, alloys thereof, including ZAMAK, etc.) which may be stamped, pressed, punched or otherwise cut from premade sheet metal. This is facilitated by the fact that in some embodiments, the applicator portion 106 is generally flat and disk-shaped, and relatively thin, similar to a washer. Manufacturing the applicator portion 106 by stamping out of sheet metal is less complex and costly than alternative manufacturing processes such as molding or die-casting, and it provides a finished part that is already electroplated on the effective surfaces, eliminating other secondary manufacturing process steps, such as electroplating which is often performed in order to prevent corrosion of the metal with molded or die-casted parts. For the above reasons, the applicator portions disclosed herein provide the added benefit of simplified manufacturing to make the applicator portion 106.

According to certain embodiments, the stone, or a plurality of stone materials, may be ground or crushed into a powder or an aggregate and then formed into a desired shape via, for example, injection molding or compression. The term "powder" is used herein with reference to relatively small particles, as opposed to "aggregate" which refers to relatively large particles. For our purposes here, both refer to smaller particles. According to certain embodiments, the powder may include granules having an average diameter of about 10 nm to about 10 micron. According to certain embodiments, an aggregate may include particles having an average diameter of at most about 10 millimeters. In some embodiments, the powder or aggregate may include granules having an average diameter from about 10 nm to about 150 microns; about 10 microns to about 10 millimeters, about 10 microns to about 100 microns; 100 microns to about 500 microns; 500 microns to about 1 millimeter; about 1 millimeter to about 5 millimeters; and/or about 5 millimeter to about 10 millimeters. In some embodiments, the powder or aggregates may include granules having an average diameter of about 10 nm, about 25 nm, about 50 nm, about 100 nm, about 150 nm, about 250 nm, about 500 nm, about 750 nm, about 1 micron, about 10 microns, about 25 microns, about 50 microns, about 100 microns, about 250 microns, about 500 microns, about 1 millimeter, about 2.5 millimeters, about 5 millimeters, and about 10 millimeters or any range of values between any two of these. However, in still other embodiments, the powder or aggregate may include granules larger or smaller than those listed. The granules may be of substantially uniform size (e.g., average diameter of about 25 microns, about 50 microns, about 250 microns, 2.5 millimeters, etc.) or size range (e.g., from about 25 microns to about 50 microns; 100 microns to about 250 microns, etc.), or the granules may include a variety of different sizes or size ranges. Moreover, the granules may be substantially uniform in shape (e.g., spherical, cubic, etc.) or may be non-uniform (e.g., randomly shaped crushed particles). Resins or other binders can be mixed with the ground stone to aid in the binding. Moreover, once the ground stone and resin/binder mixture has been molded, the resins or other binders may be removed via, for example, heat melting the resin or binder. According to certain embodiments, the stone can be coated or sealed with, for example, a polyurethane sealant, a lacquer, an ultraviolet (UV) inhibitor spray, a filler, or the like. According to still other embodiments, the stone can be polished (or roughed) to a desired surface finish.

In some implementations, the applicator portion 106 may comprise ceramics, high-density plastics, composites, or the like. Additionally, the applicator portion 106 may include one or more additional materials such as, for example, metal, plastic, glass, wood, carbon fiber, or the like. For instance, in some embodiments, metal, plastic, glass, wood, carbon fiber, or other material may be embedded in, on, or around an applicator portion 106 made initially from stone, thus making it a composite applicator portion 106. In one specific example, an applicator portion 106 may include a stone with a metal ring around at least a portion of an outer perimeter of the stone.

Referring back to FIG. 1, the applicator tip assembly 102 may further include a main body portion 108 configured to couple to the housing 104, and configured to at least partially enclose the applicator portion 106 around a periphery, or perimeter, of the applicator portion 106. With an applicator portion 106 that is generally circular, or disk-shaped, the main body portion 108 can be said to at least partially encircle the applicator portion 106, and in some implementations, such as shown in FIG. 1, the main body portion substantially encircles the applicator portion 106. The main body portion 108 may further include or define a product delivery passageway 110 extending through the main body portion 108 to convey the cosmetic or medicinal product from the reservoir 104 to exit the applicator tip assembly 102 at an application face of the applicator portion 106. In some embodiments, the product delivery passageway 110 is defined at least partially by the main body portion 108. FIG. 1 shows the main body portion 108 as having a generally cylindrical protrusion, or neck portion, extending through an aperture in the thermal storage applicator portion 106, which at least partially defines or forms the product delivery passageway 110. In some embodiments, the product delivery passageway 110 is defined by the neck portion together with the aperture in the applicator portion 106 which receives at least the neck portion of the main body portion 108.

The main body portion 108 may be made of a thermoplastic polymer, such as, for example, polypropylene, which is non-reactive with the product stored in the reservoir 104. In other implementations, the main body portion 108 may be made of plastic, metal, glass, or any other suitable material.

The dispenser 100 may also include a cap 112 that encapsulates the applicator tip assembly 102 when the dispenser 100 is not in use and includes a plug 114 that seals the product delivery passageway 110. The plug 114 may be made of a thermoplastic polymer similar to the main body portion 108 of the applicator tip assembly 102 or any other material which is non-reactive or resistant to the product being dispensed, such as various metals, plastics, ceramics, composites, or the like. Additionally or alternatively, either the plug 114, the main body portion 108, or both may be elastomeric, such that when the cap is in place either the plug 114, the main body portion 108, or both, may expand and deform somewhat to seal the product delivery passageway 110. The cap 112 is configured to couple to the housing 104, such as by use of a snap-fit attachment, a threaded attachment, a press or friction fit, one or more hinges, or any other suitable means of attachment.

Figure 2:
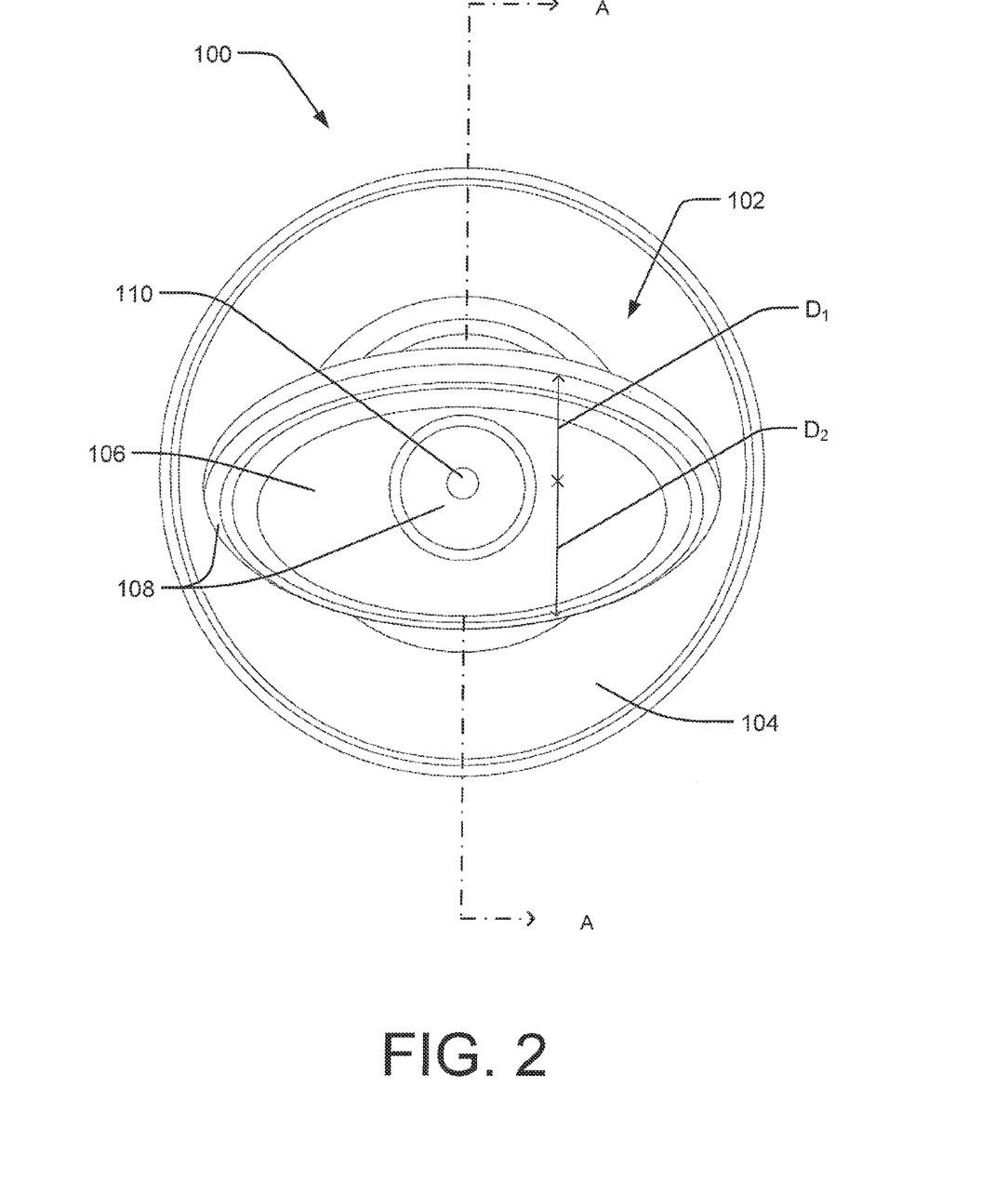
FIG. 2 is a top view of the example applicator tip assembly of the dispenser of FIG. 1.

FIG. 2 is a top view of the applicator tip assembly 102 of dispenser 100 in more detail. Again, the applicator tip assembly 102 generally comprises the applicator portion 106, the main body portion 108, and the product delivery passageway 110, which forms a dispensing path for the product in housing 104. In one implementation, the product delivery passageway 110 is positioned slightly off center within the main body portion 108. This is illustrated by the dimension lines $D_1$ and $D_2$ in FIG. 2, where $D_1$ is the distance from the topmost point of applicator tip assembly 102 to the center of the product delivery passageway 110, and $D_2$ is the distance from the bottommost point of applicator tip assembly 102 to the center of the product delivery passageway 110. As shown in the FIG. 2, $D_2$ is greater than $D_1$.

FIG. 2 further illustrates that the main body portion 108 may at least partially enclose, or encircle, the thermal storage applicator portion 106 around a periphery of the applicator portion 106. An applicator tip assembly 102 configured in this way may eliminate the need for additional manufacturing processes for making the applicator portion 106, such as secondary or finishing operations, such as deburring, buffing or polishing, for example, particularly in the case of sheet metal. When sheet metal is stamped or cut to form the applicator portion 106, these types of secondary or finishing operations would typically be required to smooth the cut, or punched, edges of the applicator portion 106. However, the main body portion 108 that encloses and surrounds the edges of the applicator portion 106 covers the possibly sharp, unfinished edges of the applicator portion 106 so that the finishing operations are not necessary or at least minimized. This is particularly beneficial for reducing the complexity and cost of manufacturing the applicator portion 106.

In FIG. 2, the thermal storage applicator portion 106 is shown as being a generally flat, disk-shaped body. In this implementation, the thermal storage applicator portion 106 is made at least in part of metal, and in the case of stainless steel, for instance, may have a mass from about 0.8 to about 3 grams. According to certain other embodiments, thermal storage applicator portions made of stone according to this disclosure may have a mass of stone of at least about 0.1 grams. According to certain other embodiments, thermal storage applicator portions according to this disclosure may have a mass of at most about 10 grams regardless of the material. In some embodiments, thermal storage applicator portions may have a mass of about 0.1 grams to about 10 grams, from about 0.1 grams to about 0.5 grams; about 0.5 grams to about 1 gram; about 1 gram to about 5 grams and/or about 5 grams to about 10 grams. In some embodiments, the thermal storage applicator portion has a mass of about 0.1 grams, about 0.5 grams, about 1.0 grams, about 3 grams, about 4 grams, about 5 grams, about 10 grams, and any range between any two of these values. However, according to still other embodiments, thermal storage applicator portions according to this disclosure may have masses smaller or larger than those listed above.

While features of various illustrative implementations are described, in other implementations, the applicator tip assembly may be configured in any form suitable for the application of the product contained in dispenser 100. For example, the applicator tip assembly may be constructed in any other suitable shape and size and may have any suitable mass, volume, and/or surface treatment desired for a given application.

Figures 3A, 3B:
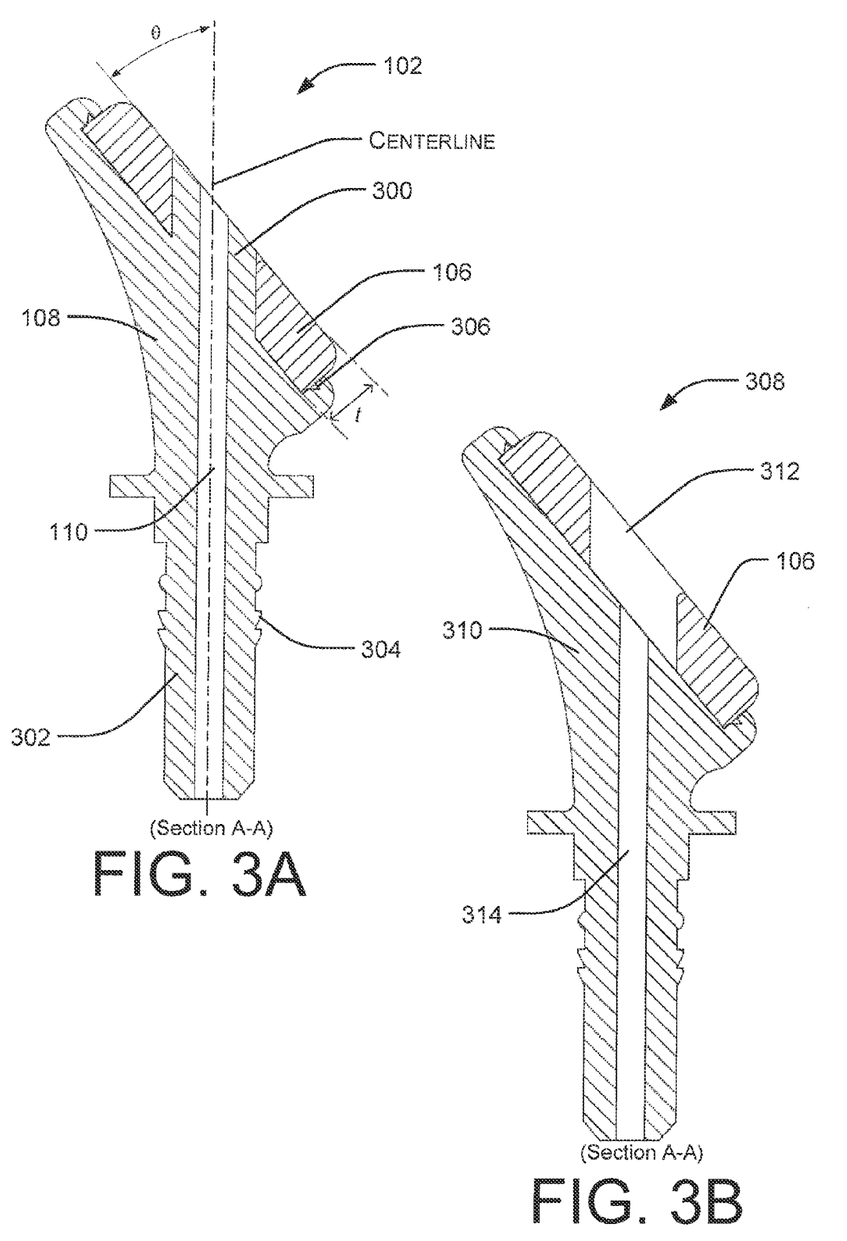
FIG. 3A is a cross-sectional view of the example applicator tip assembly of the dispenser shown in FIG. 1, taken along section line A-A of FIG. 2.
FIG. 3B is a cross-sectional view of another illustrative embodiment of an example applicator tip assembly, taken along section line A-A of FIG. 2, in which a neck portion of a main body portion is substantially omitted.

FIG. 3A illustrates the example applicator tip assembly 102 from a cross-sectional view along section line A-A of FIG. 2. The illustrative implementation shows an angle θ of the application face of the applicator portion 106 with respect to a centerline of the applicator tip assembly 102. In the illustrated implementation, the angle θ is about 60 degrees (°). This design facilitates application of the product to the user's skin. However, other designs may be used. For example, in other implementations the angle θ may be between about 30° and about 75°. According to certain embodiments, the application face may be articulable (e.g. pivotable, rotatable, etc.) relative to the applicator tip assembly 102 such that the angle of the application face with respect to a centerline of the applicator tip assembly can be changed by, for example, a user.

FIG. 3A further shows that the applicator portion 106 comprises a relatively thin member made of thermal storage material that is generally disk- or ring-shaped, similar to a washer. A thickness, t, of the applicator portion 106 may be in the range of 0.25 millimeters to 5 centimeters. Thickness may be selected based on the material and its ability to store or transfer heat energy or the feeling of coolness or warmth. Although thickness will vary by material, desired aesthetics, and application and therefore can be nearly limitless, thickness will generally be from about one millimeter to about 5 centimeters. In some embodiments, the applicator portion 106 can be about 0.25 mm, about 0.5 mm, about 0.75 mm, about 1 mm, about 1.25 mm, about 1.5 mm, about 1.75 mm, about 2 mm, about 2.5 mm, about 3 mm, about 3.5 mm, about 5 mm, about 10 mm, about 1.5 cm, about 2 cm, about 3 cm, about 4 cm, about 5 cm, or any range between any two of these values. In some embodiments, the thickness is about 1.25 mm to about 3.5 mm. In some embodiments multiple disks may be layered to achieve greater thicknesses and different properties or appearances based on the different materials.

FIG. 3A also illustrates the construction of the applicator tip assembly 102. As discussed above, the applicator tip assembly 102 includes a thermal storage applicator portion 106 made of thermal storage material that is capable of transferring and/or retaining thermal energy. The applicator tip assembly 102 may also include a main body portion 108 that at least partially encloses the applicator portion 106. For instance, FIG. 2 shows the main body portion 108 encircling the disk-shaped applicator portion 106. The main body portion 108 may include a neck portion 300, which extends through an aperture in the applicator portion 106, and a connector stem 302 usable to retain the applicator tip assembly 102 in the housing 104. The main body portion 108 may be secured to the applicator portion 106 and/or the housing 104 by, for example, a press-fit, snap-fit, adhesive, threaded fastener, and/or engagement by one or more engagement features. As such, any engagement features on the connector stem 302 may be appropriately designed and configured to enable any, or a combination of, the aforementioned means of attachment. In the illustrated implementation, the connector stem 302 of the main body portion 108 is retained in the housing 104 by a series of barbs or annular rings 304. In addition, the applicator portion 106 is shown in the illustrated implementation to be coupled to the main body portion 108 by multiple tabs 306 on a periphery, or perimeter, of the applicator portion 106 that are received into corresponding recesses in the main body portion 108 in fully assembled form.

FIG. 3B illustrates another example embodiment of an applicator tip assembly 308 as viewed from a cross-sectional view along section line A-A of FIG. 2. In the illustrative implementation, the neck portion 300 of the main body portion 108, shown in FIG. 3A, is substantially omitted so that a main body portion 310 does not extend to the upper most top, or application face, of the applicator portion 106, thereby leaving a space between the top of the main body portion 108 and the application face of the applicator portion 106. An aperture 312 of the applicator portion 106 is shown in FIG. 3B to be without the neck portion 300 of FIG. 3A disposed within the aperture 312. It is to be appreciated that, in other implementations, the neck portion 300, shown in FIG. 3A, may be formed integrally with the thermal storage applicator portion 106, may be truncated, or omitted entirely. FIGS. 3A and 3B show extreme situations, whereas in FIG. 3A, the neck portion 300 extends through the applicator portion 106, such that it is substantially flush with the surface. In contrast, FIG. 3B shows the neck portion as nearly non-existent, flush with the bottom or the applicator portion 106. In other embodiments, neck portion 300 will extend into aperture 312 partially to the surface of the applicator portion 106. (It is contemplated, that the neck portion could extend through the applicator portion 106 and beyond its surface, but such an application appears to have limited usefulness.) For example, where the product to be dispensed is not corrosive or otherwise reactive with the material of the thermal storage applicator portion 106 (or for any other desired reason), the neck portion 300 of FIG. 3A may be formed integrally with and of the same or different material as the thermal storage applicator portion 106. In that case, the thermal storage applicator portion 106 may have an aperture that is substantially the same diameter as a dispensing path 314 formed through the main body portion 310.

Figure 4:
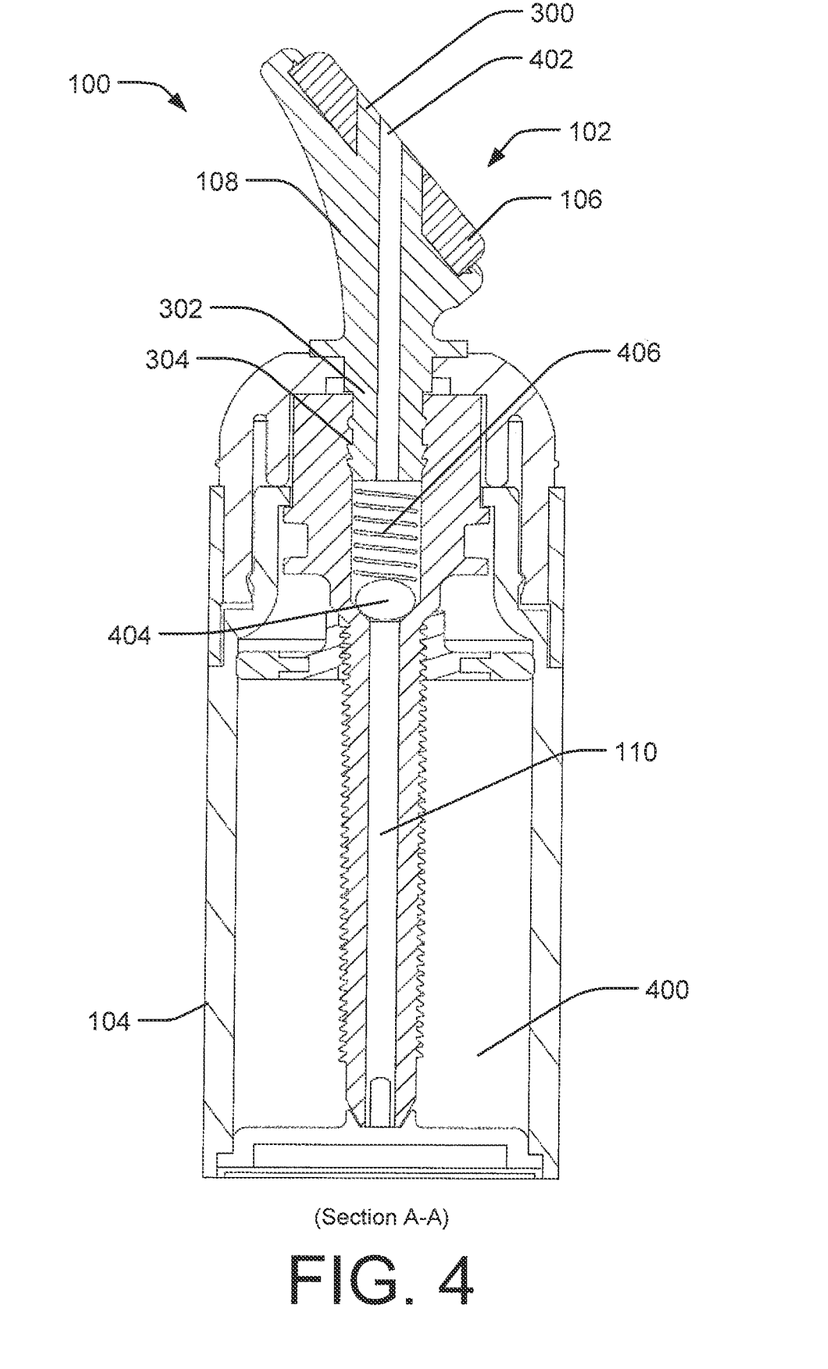
FIG. 4 is a cross-sectional view of the illustrative dispenser shown in FIG. 1, taken along line A-A of FIG. 2.

FIG. 4 is a cross-sectional view of dispenser 100, taken along section line A-A of FIG. 2, showing details of the housing 104. As shown in FIG. 4, the dispenser 100 has a reservoir 400. The product delivery passageway 110 extends from the reservoir 400, through at least part of the applicator tip assembly 102 to provide product to an opening 402 at the application face of the applicator portion 106. In some instances, the opening 402 may be defined by an opening in the neck portion 300 of the main body portion 108. The product delivery passageway 110 may define all or part of a dispensing path from the reservoir 400 to the application face of the applicator portion 106. For instance, the product delivery passageway 110 may expel the product to the application face via a aperture, bore, recess, or other passage in the applicator portion 106, such as the aperture 308 of FIG. 3B (the product delivery passageway 110 and the aperture, bore, recess, or other passage in the applicator collectively defining the dispensing path). In the illustrated implementation, the product is transported through the product delivery passageway 110 by rotating the housing 104 such that the product is dispensed through the applicator tip assembly 102 by way of a check valve comprised of a ball 404 and a spring 406. However, in other implementations, any suitable delivery mechanism may be used.

The following is a discussion of examples, without limitation, of delivery mechanisms for dispensing a product. The first example may be implemented using a click or a reverse click operation, whereby the user may operate the dispenser by moving the applicator tip assembly relative to the housing member in either a clockwise or counterclockwise direction.

Another example delivery mechanism for dispensing the product may be a squeeze operation. In certain embodiments wherein the delivery mechanism is a squeeze operation, when pressure is applied to the housing 104 containing the reservoir 400, the product in the reservoir 400 may be forced, by the squeezing action, through the dispenser 100 via a product delivery passageway for application to the user's skin.

In yet another example, a delivery mechanism for dispensing the product may be by a pressurized dispenser, such as an aerosol dispenser. In certain embodiments wherein the delivery mechanism is an aerosol delivery mechanism, the composition will be held under pressure in a container and will be dispersed along with an aerosol propellant in response to actuation by a user. Actuation may be by depressing, rotating, tilting, or otherwise manipulating the applicator tip assembly, pressing a button, and/or by any other suitable dispensing mechanism. Details of the construction and propellant of an aerosol dispenser are within the skill of one of ordinary skill in the art and will, therefore, not be described in detail herein.

In yet another example, a delivery mechanism for dispensing product may be an airless pump. The term airless pump refers to a pump that provides dispensing of a substance from a container under pressure in essentially a single direction without permitting reverse (intake) flow of air via the pump. That is, as product is pumped from the container, the pumped product is not replaced with a corresponding volume of air through the pump. In addition to preventing reverse intake flow of air, an airless pump typically does not allow intake of any other substances to replace the volume of product pumped out of the container. For example, an airless pump could include a one-way valve, such as a check valve.

As further illustrated in FIG. 4, the applicator tip assembly 102 is coupled to housing 104 by barbs 304 located on a connector stem 302 of the main body portion 108, which engage an interior of the housing 104. However, in other implementations the housing 104 may be coupled to the applicator tip assembly 102 through any suitable means. Fabrication of housing 104 and applicator tip assembly 102 may be accomplished through a separate manufacturing process, a co-molding process, or any other suitable production process.

Figure 5:
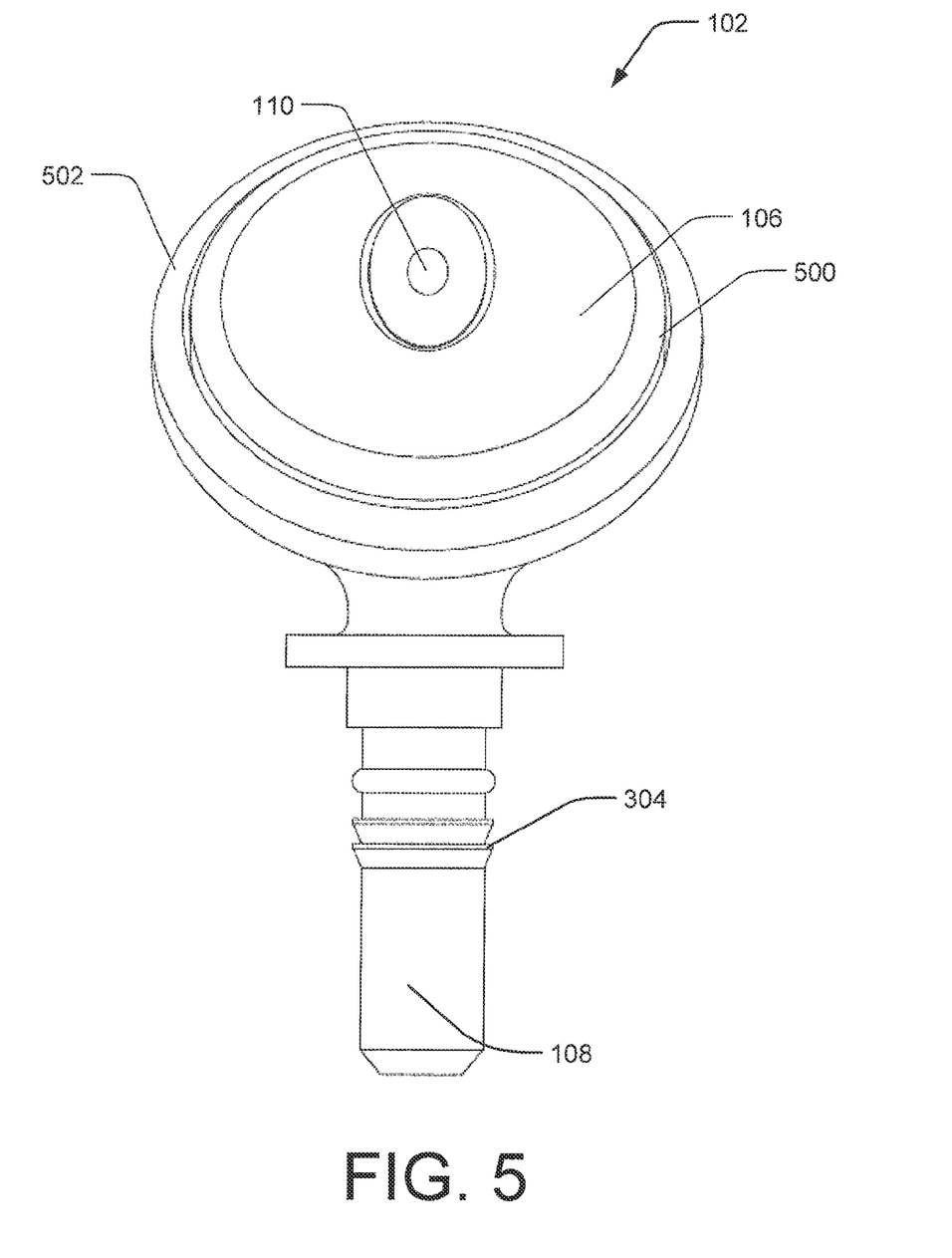
FIG. 5 is a front view of the example applicator tip assembly of the dispenser of FIG. 1.

FIG. 5 is a front view of the example applicator tip assembly 102 of the dispenser 100 of FIG. 1. FIG. 5 shows, from a front view, that the thermal storage applicator portion 106 comprises a periphery 500, or perimeter, that defines an outer edge, or edges, of the applicator portion 106. In the illustrative example of FIG. 5, the periphery 500 is circular due to the disk-shape of the applicator portion 106, but it is to be appreciated that the applicator portion 106, and therefore the periphery 500, may be of any suitable shape, such as triangular, rectangular, an irregular geometry, etc., such that the periphery 500 may be defined by a plurality of edges at various angles. In the case of FIG. 5, a singular edge defines the circular periphery 500. The main body portion 108 may further comprise an outer boundary 502 which is configured to at least partially enclose the applicator portion 106 about its periphery 500. In the case of the circular, disk-shaped applicator portion 106 of FIG. 5, the outer boundary 502 of the main body portion 108 may comprise an outer ring that encircles the applicator portion 106. As previously mentioned, by enclosing the applicator portion 106 with the outer boundary 502 of the main body portion 108, manufacturing process steps, such as deburring the edge(s) of the applicator portion 106—having been previously stamped/punched from sheet metal—can be eliminated, thereby reducing the complexity and cost of manufacturing the applicator portion 106.

Figure 6:
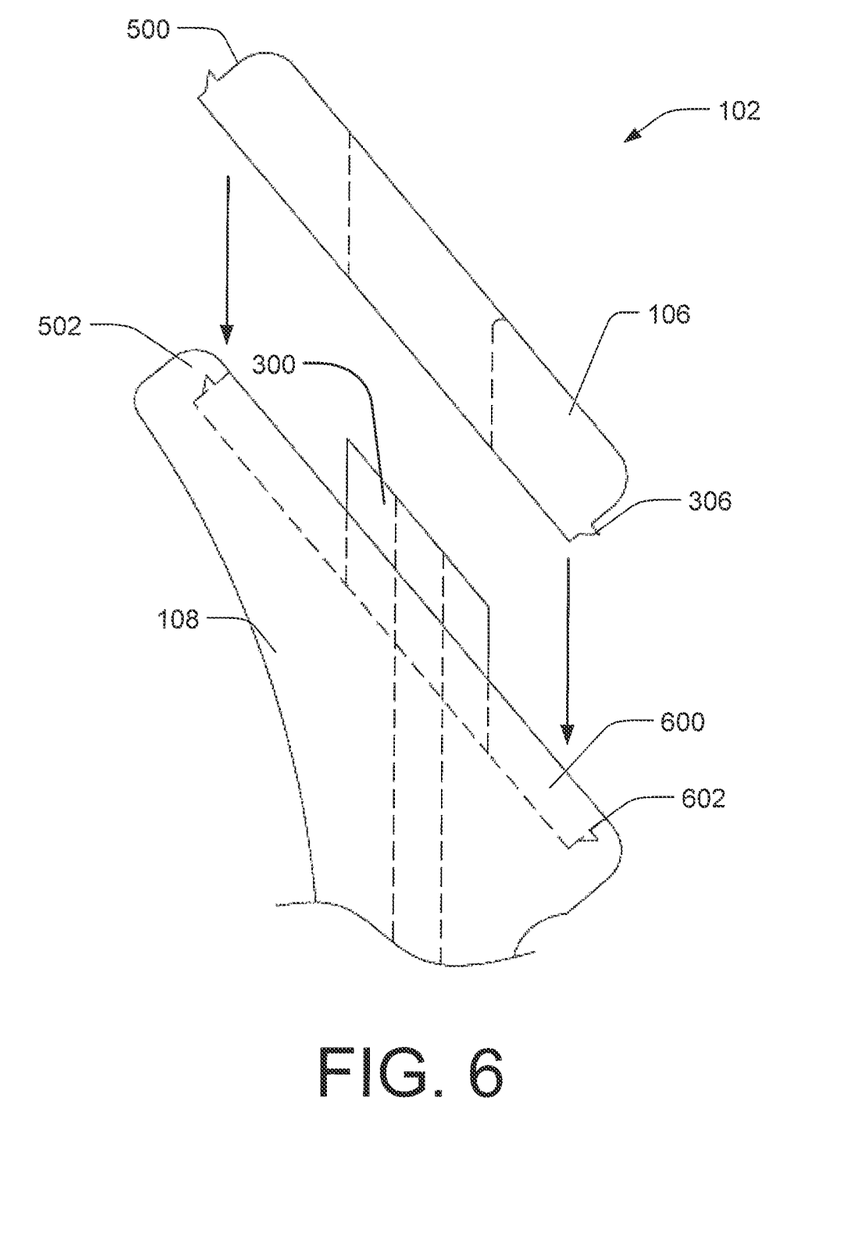
FIG. 6 is a partial exploded, side view of the example applicator tip assembly of the dispenser of FIG. 1.

FIG. 6 is a partial exploded, side view of the applicator tip assembly 102 of the dispenser 100 of FIG. 1. Before full assembly, the applicator tip assembly 102 comprises at least two main separate parts; the thermal storage applicator portion 106 and the main body portion 108. The thermal storage applicator portion 106 may be coupled to the main body portion by being received in a recess 600 of the main body portion 108 such that the outer boundary 502 of the main body portion 108 at least partially encloses the periphery 500 of the thermal storage applicator portion 106. The multiple tabs 306 on the periphery 500 of the applicator portion 106 are configured to be received within corresponding notches 602, or recesses, in the outer boundary 502 of the main body portion 108 when the two component parts of the applicator tip assembly 102 are coupled together in fully assembled form.

Additional Example Applicator Tip Assemblies for a Dispenser

Figure 7A:
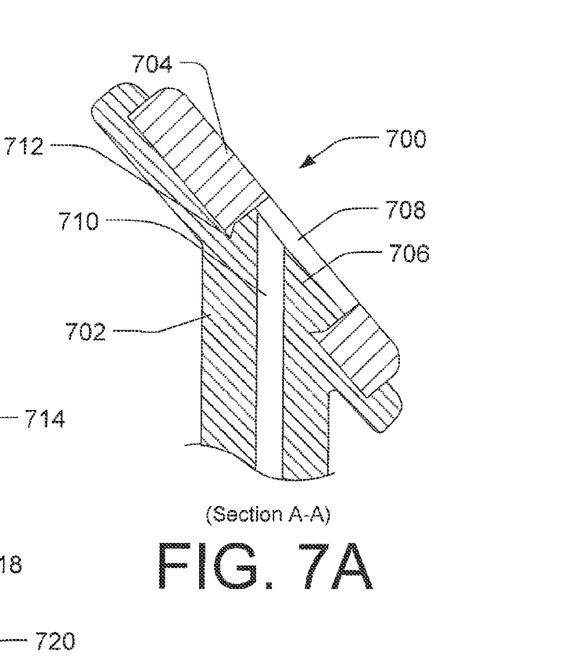
FIG. 7A is a cross-sectional view of an example applicator tip assembly according to another illustrative embodiment, taken along section line A-A of FIG. 2, in which a main body portion of the applicator tip assembly includes a neck portion that is substantially perpendicular to an application face.
Figure 7B:
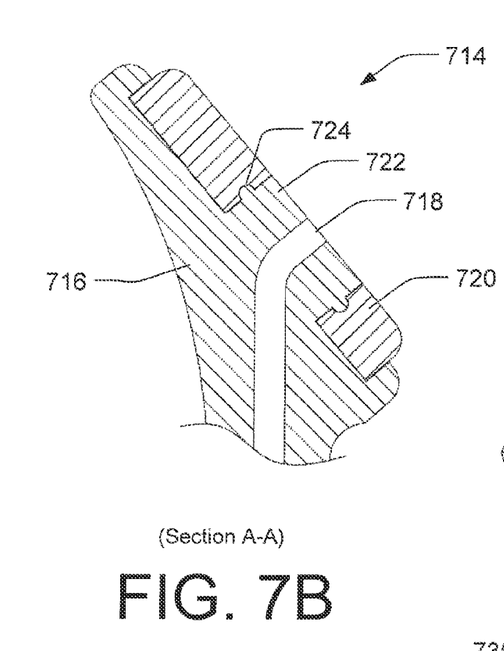
FIG. 7B is a cross-sectional view of an example applicator tip assembly according to another illustrative embodiment, taken along section line A-A of FIG. 2, in which a main body portion of the applicator tip assembly includes a curved delivery passageway.
Figure 7C:
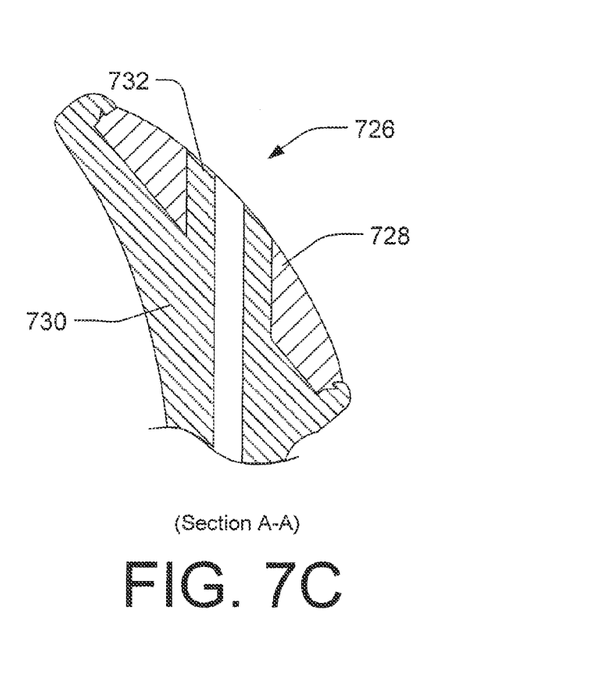
FIG. 7C is a cross-sectional view of an example applicator tip assembly according to another illustrative embodiment, taken along section line A-A of FIG. 2, in which the applicator tip assembly has a generally convex shape at an application face.

FIGS. 7A-7C illustrate cross-sectional views of applicator tip assemblies according to other illustrative embodiments, taken along section line A-A of FIG. 2. FIG. 7A shows an applicator tip assembly 700 comprising a main body portion 702, and a thermal storage applicator portion 704 coupled to the main body portion 702. The main body portion 702 may comprise a neck portion 706 which protrudes substantially perpendicular to a plane of an application face of the applicator portion 704. The applicator portion 704 may have a correspondingly perpendicular aperture 708 to receive the neck portion 706 when coupled to the main body portion 702. The delivery passageway 710 may extend through the main body portion 702 to provide an exit for the product in the dispenser to exit at the application face of the applicator portion 704. Additionally, the neck portion 706 may have recesses 712 configured to receive corresponding protrusions or tabs in the applicator portion 704 to facilitate coupling of the applicator portion 704 to the main body portion 702.

FIG. 7B shows an applicator tip assembly 714 in which a main body portion 716 of the applicator tip assembly 714 includes a curved delivery passageway 718. The delivery passageway 718 may extend through the main body portion 716 in a curved manner to provide an exit for the product in the dispenser to exit at the application face of an applicator portion 720. Additionally, the main body portion 716 may comprise a neck portion the neck portion 722 comprising protruding tabs 724 configured to mate with corresponding recessed notches in the applicator portion 720 on the inside of the aperture of the applicator portion 720. In some implementations, the tabs 724 may be replaced with a singular, ring protrusion that is received within a ring-shaped slot in the applicator portion 720.

FIG. 7C shows an applicator tip assembly 726 which has a generally convex shape at an application face. Accordingly, an applicator portion 728 may be generally convex and disk-shaped. A main body portion 730 may have neck portion 732 with a correspondingly curved surface at the application face such that the application face of the applicator tip assembly 726 is smooth between the surface portions of the applicator portion 728 and the neck portion 732 of the main body portion 730. The applicator portion 728 may be coupled to the main body portion 730 in any of the aforementioned techniques described herein. Additionally, the applicator portion 728 may be coupled to the main body portion 730 by, for example, press fit, adhesive, snap fit, one or more ribs or barbs, or any other suitable fastening means.

In one example, the applicator portions 704, 720, 728 may have a mass from about 0.1 grams to about 3 grams and a volume from about 0.1 centimeters$^3$ to about 0.5 centimeters$^3$. However, in other examples, the applicator portions may have volumes and/or masses larger or smaller than the examples given.

Alternative Illustrative Dispenser with an Applicator Tip Assembly

In the implementations shown in FIGS. 1-7, the applicator tip assembly is shown as having a generally flat (FIGS. 1-7B) or convex (FIG. 7C), disk-shaped body. However, in other implementations, applicator tip assemblies may take any other desired form, such as generally spherical, elliptical, curvilinear, parabolic, flat, trapezoidal, combinations of the foregoing, or the like.

Figure 8:
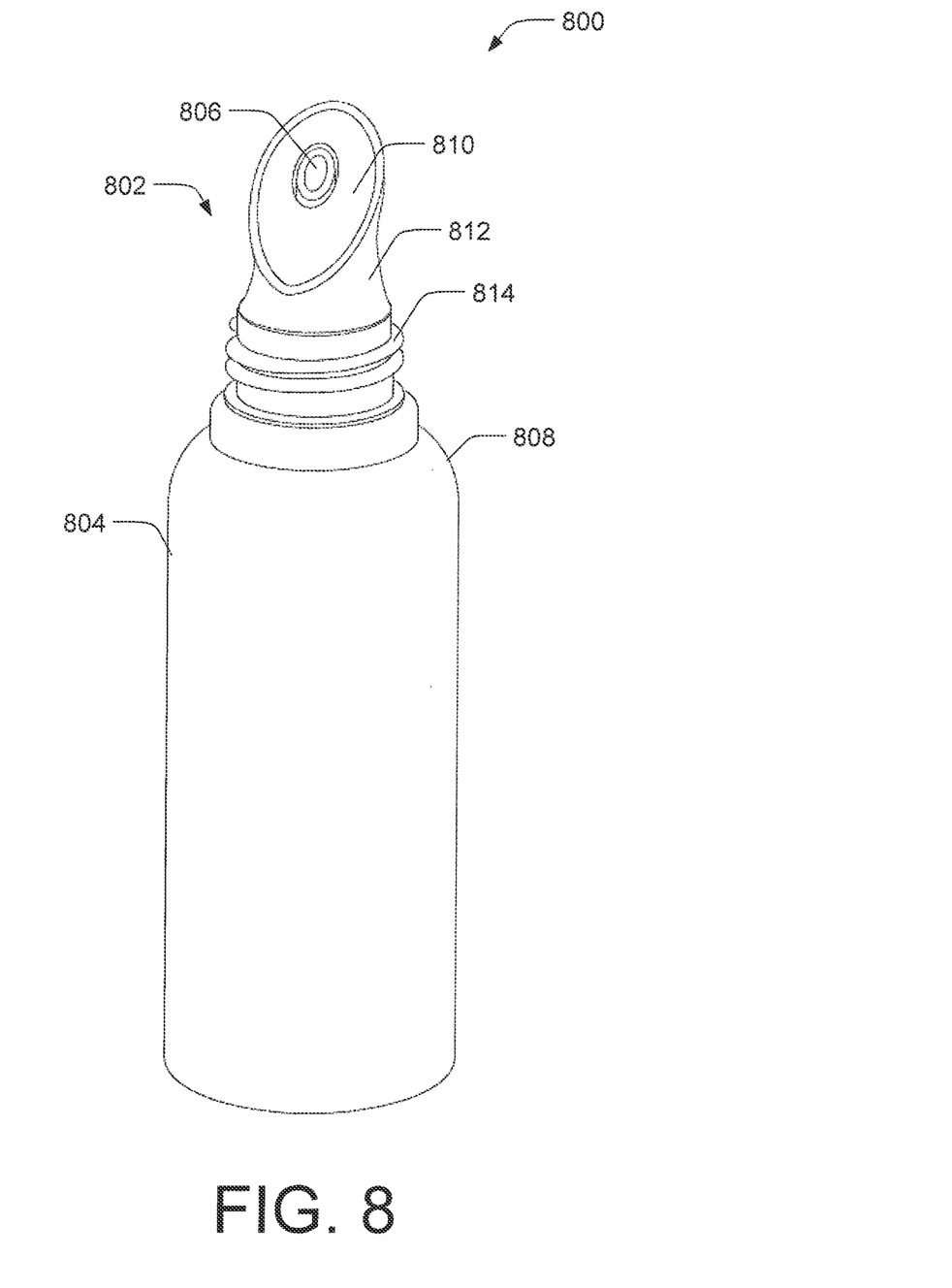
FIG. 8 is a perspective view of another dispenser with an example applicator tip assembly according to another illustrative embodiment in which the applicator tip assembly is generally egg-shaped at an application face.

FIG. 8 shows an alternative dispenser 800 with an applicator tip assembly 802 according to another illustrative embodiment in which the applicator tip assembly 802 is generally elliptical or egg-shaped at an application face. The dispenser 800 includes the applicator tip assembly 802 and a housing 804 with a reservoir. In particular, the housing 804 shown in the illustrative implementation is a flexible tube that may be squeezed to dispense product from a dispensing path 806 through the applicator tip assembly 802.

The applicator tip assembly 802 may be coupled to the housing 804 by placing the applicator tip assembly 802 over a narrowed neck 808 of the housing 804 and attaching it to the housing 804 by, for example, crimping, adhesive, press-fit, snap-fit, retaining ribs or barbs on the inside of the applicator tip assembly and/or the outside of the narrowed neck of the housing, and/or by any other suitable attachment means. The applicator tip assembly may comprise a thermal storage applicator portion 810 that is generally egg- or elliptical shaped and configured to couple to a main body portion 812. In some embodiments, the dispenser 800 may further include a cap, such as the cap 112 of FIG. 1, that encapsulates the applicator tip assembly 802 when the dispenser 800 is not in use, and may include a plug, such as the plug 114 of FIG. 1, that seals the product delivery passageway 806. FIG. 8 illustrates exemplary threads 814 that may be configured to provide the cap with a means of attachment to the housing 804, such that the cap may be twisted onto the housing 804 in order to couple the cap to the housing 804. It is to be appreciated that other means of attachment, such as by use of a snap-fit attachment, a press or friction fit, one or more hinges, etc., may be utilized for coupling the cap to the housing 804 of the dispenser 800.

In still other implementations, dispenser may additionally or alternatively include a brush, a sponge, or various other features to assist in the application of a dispensed product to a user's skin.

While the dispensers with applicator tip assemblies shown in FIGS. 1-8 are comprised of a separate applicator tip assembly and housing, in other implementations to decrease manufacturing costs, or for any other desired reason, some or all of the applicator tip assembly and some or all of the housing may be formed integrally. In still other implementations, application devices or implements may be configured with an applicator tip assembly as disclosed herein to apply cosmetic product, while omitting a reservoir for holding the cosmetic product. For instance, such an application device or implement may be dipped in a pot or reservoir of product to pick up the product for application to the skin or other surface.

Conclusion

Although the invention has been described in language specific to structural features and/or methodological acts, it is to be understood that the invention is not necessarily limited to the specific features or acts described. Rather, the specific features and acts are disclosed as illustrative forms of implementing the invention.

What is claimed is:

1. An applicator device comprising:
a housing having a reservoir for containing a cosmetic or medicinal product; and
an applicator tip assembly comprising:
a main body portion coupled to the housing and comprising a product delivery passageway extending through the main body portion to convey the cosmetic or medicinal product, the main body portion forming a surface of the product delivery passageway that contacts the product, and
a thermal storage applicator portion coupled to the main body portion and enclosed by the main body portion at a periphery of the thermal storage applicator portion, the thermal storage applicator portion having an application face for applying the cosmetic or medicinal product to a surface.

2. The applicator device of claim 1, wherein the thermal storage applicator portion comprises at least one of metal, ceramic, or stone material configured to store and/or transfer thermal energy.

3. The applicator device of claim 1, wherein the main body portion comprises a thermoplastic polymer.

4. The applicator device of claim 3, wherein the thermoplastic polymer comprises polypropylene.

5. The applicator device of claim 1, wherein the main body portion and the housing may be integrally formed.

6. The applicator device of claim 1, wherein the main body portion and the housing are formed separately and sealingly coupled together.

7. The applicator device of claim 1, wherein the thermal storage applicator portion is generally disk-shaped with an aperture defined therein.

8. The applicator device of claim 7, wherein the thermal storage applicator portion is generally convex on the application face.

9. The applicator device of claim 7, wherein main body portion further comprises a neck portion that extends through the aperture defined in the thermal storage applicator portion.

10. The applicator device of claim 1, wherein the applicator tip assembly is fixed to the housing against movement relative to the housing.

11. The applicator device of claim 1, wherein the thermal storage applicator portion comprises a thickness in a range of 1.25 millimeters to 3.5 millimeters.

12. The applicator device of claim 1, wherein a product delivery passageway is curved along at least part of the product delivery passageway.

13. The applicator device of claim 1, further comprising a product delivery mechanism to dispense the cosmetic or medicinal product from the reservoir, the product delivery mechanism comprising:
a reverse click motion delivery mechanism;
a click motion delivery mechanism;
a squeeze tube delivery mechanism;
an airless pump delivery mechanism; or
an aerosol delivery mechanism.

14. A dispenser comprising:
a housing having a reservoir for containing a product; and
an applicator tip assembly comprising:
a main body portion coupled to the housing and having a product delivery passageway extending through the main body portion, the main body portion forming a surface of the product delivery passageway that contacts the product, and
a thermal storage applicator portion coupled to, and at least partially enclosed by, the main body portion, the thermal storage applicator portion comprising an application face for applying the product to a surface.

15. The dispenser of claim 14, wherein the thermal storage applicator portion comprises at least one of metal, ceramic, or stone.

16. The dispenser of claim 14, wherein the thermal storage applicator portion comprises stainless steel.

17. The dispenser of claim 14, wherein the applicator tip assembly is fixed to the housing against movement relative to the housing.

18. The dispenser of claim 14, wherein the thermal storage applicator portion is generally disk-shaped with an aperture defined therein.

19. The dispenser of claim 14, wherein main body portion comprises a thermoplastic polymer.

20. The dispenser of claim 19, wherein the thermoplastic polymer comprises polypropylene.

21. The dispenser of claim 14, wherein the thermal storage applicator portion is substantially enclosed by the main body portion at a periphery of the thermal storage applicator portion.

22. A dispenser comprising:
a housing having a reservoir for containing a product; and an applicator tip assembly coupled to the housing, the applicator tip assembly comprising:
  an applicator portion made of thermal storage material and comprising an application face with an aperture therein for applying a product to a surface; and
  a main body portion configured to at least partially enclose the applicator portion around a periphery of the applicator portion, the main body portion comprising a delivery passageway configured to convey the product from the reservoir to the application face via the aperture in the application face, the main body portion forming a surface of the product delivery passageway that contacts the product.

23. The dispenser of claim 22, wherein the main body portion is made of a thermoplastic polymer.

24. The dispenser of claim 22, wherein the applicator portion comprises metal.

25. The dispenser of claim 22, wherein the main body portion substantially encloses the applicator portion around a periphery of the applicator portion.

26. The dispenser of claim 22, wherein the applicator portion is generally flat and disk-shaped.

27. An applicator tip assembly comprising:
  a main body portion adapted to be coupled to a housing and at least partially defining a product delivery passageway extending through the main body portion to convey a product stored in the housing, the main body portion forming a surface of the product delivery passageway that contacts the product, and
  a thermal storage applicator portion coupled to the main body portion and enclosed by the main body portion at a periphery of the thermal storage applicator portion, the thermal storage applicator portion having an application face for applying the product to a surface.

28. The applicator device of claim 27, wherein the thermal storage applicator portion comprises at least one of metal, ceramic, or stone material configured to store and/or transfer thermal energy.

* * * * *